(12) United States Patent
Amith et al.

(10) Patent No.: US 9,814,711 B2
(45) Date of Patent: Nov. 14, 2017

(54) ANTITUBERCULAR COMPOSITION COMPRISING RIFAMPICIN, ISONIAZID, ETHAMBUTOL AND PYRAZINAMIDE AND ITS PROCESS OF PREPARATION

(71) Applicant: SANOFI, Paris (FR)

(72) Inventors: Kumar Amith, Gurdaspur (IN); Madavan Bindu, Paris (FR); Prasad Kum, Hyderabad (IN); Khullar Praveen, Dona Paula (IN)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/906,870

(22) PCT Filed: Jul. 22, 2014

(86) PCT No.: PCT/EP2014/065763
§ 371 (c)(1),
(2) Date: Jan. 21, 2016

(87) PCT Pub. No.: WO2015/011163
PCT Pub. Date: Jan. 29, 2015

(65) Prior Publication Data
US 2016/0158226 A1   Jun. 9, 2016

(30) Foreign Application Priority Data
Jul. 26, 2013 (IN) .............. 3343/CHE/2013

(51) Int. Cl.
*A61K 31/496* (2006.01)
*A61K 9/20* (2006.01)
*A61K 31/133* (2006.01)
*A61K 31/4409* (2006.01)
*A61K 31/4965* (2006.01)

(52) U.S. Cl.
CPC .......... *A61K 31/496* (2013.01); *A61K 9/2027* (2013.01); *A61K 9/2054* (2013.01); *A61K 9/2077* (2013.01); *A61K 9/2081* (2013.01); *A61K 31/133* (2013.01); *A61K 31/4409* (2013.01); *A61K 31/4965* (2013.01)

(58) Field of Classification Search
CPC .................... A61K 9/2077; A61K 9/2081
See application file for complete search history.

(56) References Cited

U.S. PATENT DOCUMENTS

| 7,195,769 B2 | 3/2007 | Singh et al. |
| 2005/0059719 A1 | 3/2005 | Badawy et al. |
| 2012/0027853 A1 | 2/2012 | Pao et al. |
| 2016/0158157 A1 | 6/2016 | Dilip et al. |
| 2016/0184231 A1 | 6/2016 | Dilip et al. |

FOREIGN PATENT DOCUMENTS

| CN | 1217912 A | 6/1999 |
| CN | 1857280 A | 11/2006 |
| CN | 1989966 B | 6/2011 |
| KR | 2010-0090138 A | 8/2010 |
| WO | WO-02/11728 A2 | 2/2002 |
| WO | WO-02/087547 A1 | 11/2002 |
| WO | WO-2007/043542 A1 | 4/2007 |
| WO | WO-2011/012987 A1 | 2/2011 |
| WO | WO-2012/013756 A2 | 2/2012 |
| WO | WO-2015/011161 A1 | 1/2015 |
| WO | WO-2015/011162 A1 | 1/2015 |

OTHER PUBLICATIONS

International Search Report mailed on Oct. 15, 2014, for PCT Application No. PCT/EP2014/065763, filed Jul. 22, 2014, three pages.
Written Opinion mailed on Oct. 15, 2014, for PCT Application No. PCT/EP2014/065763, filed Jul. 22, 2014, six pages.
Lupin Ltd. (Jan. 2013). Medical Prescription of Akurit Kid Dosage & Drug Information, CIMS India, retrieved from the internet on May 5, 2017, two pages.
Prasad, B. et al. (Jun. 16, 2006; e-pub. Apr. 18, 2006). "Study of the Interaction Between Rifapentine and Isoniazid Under Acid Conditions," *J. Pharm. Biomed. Anal.* 41(4):1438-1441.
Zumla, A. et al. (Jun. 27, 1998). "Tuberculosis." *BMJ* 316(7149):1962-1964.
International Search Report and Written Opinion dated Sep. 25, 2014, for PCT Application No. PCT/EP2014/065762, filed Jul. 22, 2014, eight pages.
International Search Report dated Sep. 25, 2014, for PCT Application No. PCT/EP2014/065761, filed Jul. 22, 2014, four pages.
Written Opinion dated Sep. 25, 2014, for PCT Application No. PCT/EP2014/065761, filed Jul. 22, 2014, four pages.
U.S. Appl. No. 14/906,876, with an international filed Jul. 22, 2014, also published as US-2016/0158157-A1.
U.S. Appl. No. 14/906,885, with an international filed Jul. 22, 2014, also published as US-2016/0184231-A1.

*Primary Examiner* — Carlos Azpuru
(74) *Attorney, Agent, or Firm* — Morrison & Foerster LLP

(57) ABSTRACT

The present invention relates to a monolayer tablet for use in the treatment of tuberculosis comprising a mixture of: —granules comprising isoniazid, pyrazinamide, ethambutol or a pharmaceutically acceptable salt thereof and at least one granulation binder, —rifampicin in powder form, —extragranular excipients, wherein all of the granules have a particle size that is less than 0.599 mm, preferably less than 0.5 mm, more preferably less than 0.422 mm, and to its process of preparation.

20 Claims, No Drawings

ANTITUBERCULAR COMPOSITION COMPRISING RIFAMPICIN, ISONIAZID, ETHAMBUTOL AND PYRAZINAMIDE AND ITS PROCESS OF PREPARATION

CROSS REFERENCE TO RELATED APPLICATIONS

This application is a National Phase application under 35 U.S.C. §371 of International Application No. PCT/EP2014/065763, filed Jul. 22, 2014, which claims priority benefit to Indian Application No. 3343/CHE/2013, filed Jul. 26, 2013, the disclosures of each of which are herein incorporated by reference in their entirety.

INTRODUCTION

The present invention relates to a stable anti-tuberculosis drug composition in the form of a monolayer tablet comprising four active agents, namely rifampicine, isoniazid, pyrazinamide, ethambutol or a pharmaceutically acceptable salt thereof.

Tuberculosis is an infectious disease that is caused by bacillus *Mycobacterium tuberculosis*. It typically affects the lungs but can affect other sites as well. According to the WHO, approximately one-third of the world's population is infected with this disease. Developing countries in Asia and Africa account for the majority of the number of infections. In 2011, there were an estimated 8.7 million incident cases of tuberculosis worldwide.

Emergence of drug resistant tuberculosis is a major public health concern because it threatens the future success of tuberculosis control. Drug resistance in tuberculosis patients is mostly due to poor patient compliance with the treatment. When using single drug compositions, the patient is required to consume 6 to 8 tablets at a time on an empty stomach everyday. Failure to comply with the treatment in its entirety leads to the development of multi-drug resistant strains of tuberculosis.

In order to control the emergence of drug resistant tuberculosis, the WHO recommends the use of fixed dose combinations (FDC) in the form of tablets which comprise, in the same formulation, four different active agents, namely rifampicine, isoniazid, pyrazinamide and ethambutol in fixed proportions.

However, the preparation and use of such FDCs present the following drawbacks:
 the size of the tablet is very big and makes it difficult to swallow for the patients;
 the bioavailability of rifampicin can be unsatisfactory due to its poor solubility in water, to a change of its crystallographic form during tabletting and to its incompatibility with the three other actives, especially with isoniazid.

One way to prevent undesirable interactions between the active agents is to physically separate the actives by introducing each incompatible active in a different layer or by granulating the incompatible actives separately.

US 2012/0027853 in the name of TAIWAN BIOTECH CO., LTD discloses a process for the preparation of a composition comprising rifampicine, isoniazid, pyrazinamide and ethambutol in the form of a bilayer tablet wherein isoniazid and rifampicine are in separate layers.

WO 02/087547 in the name of LUPIN LABORATORIES LIMITED discloses a process for the preparation of an antitubercular composition comprising rifampicin, ethambutol, isoniazid and pyrazinamide in the form of a monolayer tablet wherein the four actives are each granulated separately or wherein rifampicin and pyrazinamide are granulated separately and isoniazid and ethambutol are granulated together.

The compositions and processes disclosed in these applications are not satisfying because they require complex preparation processes with many different steps which are time and energy consuming.

WO 02/11728 in the name of PANACEA BIOTECH LIMITED discloses an antitubercular composition comprising rifampicin, ethambutol, isoniazid and pyrazinamide in the form of an effervescent monolayer tablet wherein isoniazid, pyrazinamide and ethambutol are in powder form whereas rifampicine is in the form of an enteric-coated granule. However, the presence of an enteric coating adds extra costs and the bioavailability of the enteric-coated active differs from the bioavailability of the release of the active in the stomach.

WO 2012/013756 in the name of LABORATOIRES PHARMA discloses a process for the preparation of an antitubercular composition comprising rifampicin, ethambutol, isoniazid and pyrazinamide in the form of a monolayer tablet wherein isoniazid, pyrazinamide and ethambutol are granulated together and rifampicine is in powder form. However, this application fails to disclose important parameters such as the quantities of excipients and the size of the resulting tablet.

As such, there remains a need for an antitubercular composition in the form of a monolayer tablet comprising rifampicine, isoniazid, pyrazinamide, ethambutol or a pharmaceutically acceptable salt thereof, that responds to the following criteria:
 the size of the tablet is as small as possible in order to facilitate its ingestion by the patient;
 the composition is stable overtime;
 the bioavailability of each active ingredient is acceptable in view of WHO standards;
 the process of preparation is simple and cost-effective;
 the quantity of impurity due to the undesirable interaction between rifampicin and isoniazid (3-formyl-rifampicin-isoniazid adduct) in the coated tablet is less than 1% after 2 months of aging at 40° C. and 75% of relative humidity.

Applicant has discovered that the provision of such a tablet can be rendered possible by granulating isoniazid, pyrazinamide and ethambutol together and by adding rifampicine in its powder form extragranularly, by reducing the size of the granules and by reducing the amount of excipients used in the granules as well as in the extragranular matrix.

Invention

A first object of the present invention is a monolayer tablet for use in the treatment of tuberculosis said tablet comprising a mixture of:
 granules comprising isoniazid, pyrazinamide, ethambutol or a pharmaceutically acceptable salt thereof and at least one granulation binder,
 rifampicine in powder form,
 extragranular excipients,
wherein all of the granules have a particle that is size less than 0.599 mm, preferably less than 0.5 mm, more preferably less than 0.422 mm.

Another object of the present invention is a process for the preparation of a tablet according to the present invention, said process comprising a step of a) wet-granulating isoniazid, pyrazinamide and ethambutol with an aqueous solution of a granulation binder to obtain granules.

The composition according to the present invention is in the form of a monolayer tablet suitable for oral administration for the treatment of tuberculosis.

According to a specific embodiment, the tablet exhibits a mass that is less than 1100 mg, preferably from 850 to 1075 mg and more preferably from 1000 to 1055 mg.

The monolayer tablet comprises four active agents, namely rifampicine, isoniazid, pyrazinamide and ethambutol or a pharmaceutically acceptable salt thereof.

In a particular embodiment, the rifampicine that is introduced in the composition according to the present invention exhibits a density of between 0.3 and 1, preferably between 0.4 and 0.8 and more preferably 0.5.

In a specific embodiment, ethambutol is introduced in the composition in the form of a pharmaceutically acceptable salt thereof, such as ethambutol hydrochloride or ethambutol hydrobromide, preferably ethambutol hydrochloride. In all that follows, the term ethambutol can mean ethambutol or a pharmaceutically acceptable salt thereof.

Preferably, the tablet comprises 75 mg of isoniazid, 400 mg of pyrazinamide, 275 mg of ethambutol hydrochloride and 150 mg of rifampicine.

The composition according to the present invention comprises granules that are dispersed in an extragranular matrix. The granules comprise three active agents, namely isoniazid, pyrazinamide and ethambutol as well as a granulation binder.

All of the granules of the composition according to the present invention exhibit a particle size that is less than 0.599 mm, preferably less than 0.5 mm, more preferably less than 0.422 mm.

According to a specific embodiment, all of the granules exhibit a particles size that is more than 0.075 mm, preferably more than 0.08 mm, more preferably more than 0.085 mm.

According to the present invention a particle size that is less than a specific value is the sieve size through which the granules can pass and may be measured according to the test method described herein.

According to the present invention a particle size that is more than a specific value is the sieve size through which the granules are retained and may be measured according to the test method described herein.

According to the present invention, the expression "all of the granules" intends to mean 95%±5% w/w of granules in the composition.

The granulation binder is dissolved in water prior to mixing with the three actives in powder form to form granules by wet-granulation. The use of a binder allows the formation of resistant granules that will not fall apart once they are dried due to the formation of bonds between the binder and the actives. Granulation binders are selected in the group consisting of povidone (polyvinylpyrrolidone), polyvinyl alcohol, maize starch, pregelatinized starch. According to a preferred embodiment, the granulation binder is povidone. The composition according to the present invention may comprise from 0.1 to 2%, preferably from 0.5 to 1.5%, more preferably from 0.9 to 1% w/w of granulation binder.

Unless mentioned otherwise, in the preceding paragraph and in the following paragraphs, the percentages are expressed in weight with respect to the total weight of the tablet.

The extragranular matrix comprises the fourth active agent, namely rifampicine, as well as extragranular excipients. The extragranular excipients comprise at least a disintegrant agent. Further extragranular excipients can be selected from a diluent, a lubricant, a flavouring agent, a colorant, or mixtures thereof. In a particular embodiment, the extragranular excipients comprise a disintegrant, a diluent, a lubricant and an antioxidant. According to a specific embodiment, the composition according to the present invention comprises from 10 to 17%, preferably from 11 to 15%, even more preferably from 12.8 to 13.3% w/w of extragranular excipients.

Examples of suitable diluents are microcrystalline cellulose, pregelatinized starch, dicalcium phosphate. Preferably, the diluent is microcrystalline cellulose. According to a specific embodiment, the composition according to the present invention comprises from 6 to 12%, preferably from 7 to 10%, even more preferably from 8.1 to 8.6% w/w of diluent.

Examples of suitable disintegrants are croscarmellose sodium, crospovidone, pregelatinized starch, maize starch, low substituted hydroxypropyl cellulose, alginic acid. Preferably, the disintegrant agent is croscarmellose sodium. According to a specific embodiment, the composition according to the present invention comprises from 2 to 6%, preferably from 3 to 5%, even more preferably from 3.6 to 3.9% w/w of disintegrant.

The lubricant is in solid form and is selected from magnesium stearate, sodium stearylfumarate, calcium stearate, stearic acid, zinc stearate, glyceryl behanate. Preferably, the lubricant is magnesium stearate. According to a specific embodiment, the composition according to the present invention comprises from 0.1 to 2%, preferably from 0.2 to 1%, even more preferably from 0.4 to 0.5% w/w of lubricant.

The antioxidant is in solid form and is selected from sodium ascorbate, 2,6-di-tert-butyl-4-hydroxytoluene (BHT), citric acid, tocopherol, sodium metabisulfite. Preferably, the antioxidant is sodium ascorbate. According to a specific embodiment, the composition according to the present invention comprises from 0.1 to 2%, preferably from 0.2 to 1%, even more preferably from 0.5 to 0.6% w/w of antioxidant.

According to an embodiment, the extragranular excipients of the tablet comprise:
- from 6 to 12%, preferably from 7 to 10%, even more preferably from 8.1 to 8.6% w/w of diluent;
- from 2 to 6%, preferably from 3 to 5%, even more preferably from 3.6 to 3.9% w/w of disintegrant;
- from 0.1 to 2%, preferably from 0.2 to 1%, even more preferably from 0.4 to 0.5% w/w of lubricant; and
- from 0.1 to 2%, preferably from 0.2 to 1%, even more preferably from 0.5 to 0.6% w/w of antioxidant.

According to another embodiment, the extragranular excipients of the tablet comprise:
- from 6 to 12%, preferably from 7 to 10%, even more preferably from 8.1 to 8.6% w/w of microcrystalline cellulose;
- from 2 to 6%, preferably from 3 to 5%, even more preferably from 3.6 to 3.9% w/w of croscarmellose sodium;
- from 0.1 to 2%, preferably from 0.2 to 1%, even more preferably from 0.4 to 0.5% w/w of magnesium stearate; and
- from 0.1 to 2%, preferably from 0.2 to 1%, even more preferably from 0.5 to 0.6% w/w of sodium ascorbate.

According to an embodiment, the tablet comprises:
- 75 mg of isoniazid,
- 400 mg of pyrazinamide,
- 275 mg of ethambutol hydrochloride
- from 0.1 to 2%, preferably from 0.5 to 1.5%, more preferably from 0.9 to 1% w/w of granulation binder, wherein isoniazid, pyrazinamide, ethambutol hydrochloride and the granulation binder are in the form of granules;
- 150 mg of rifampicin;

from 6 to 12%, preferably from 7 to 10%, even more preferably from 8.1 to 8.6% w/w of diluent;
from 2 to 6%, preferably from 3 to 5%, even more preferably from 3.6 to 3.9% w/w of disintegrant;
from 0.1 to 2%, preferably from 0.2 to 1%, even more preferably from 0.4 to 0.5% w/w of lubricant; and
from 0.1 to 2%, preferably from 0.2 to 1%, even more preferably from 0.5 to 0.6% w/w of antioxidant.

According to another embodiment, the tablet comprises:
75 mg of isoniazid,
400 mg of pyrazinamide,
275 mg of ethambutol hydrochloride
from 0.1 to 2%, preferably from 0.5 to 1.5%, more preferably from 0.9 to 1% w/w of povidone, wherein isoniazid, pyrazinamide, ethambutol hydrochloride and povidone are in the form of granules;
150 mg of rifampicin;
from 6 to 12%, preferably from 7 to 10%, even more preferably from 8.1 to 8.6% w/w of microcrystalline cellulose;
from 2 to 6%, preferably from 3 to 5%, even more preferably from 3.6 to 3.9% w/w of croscarmellose sodium;
from 0.1 to 2%, preferably from 0.2 to 1%, even more preferably from 0.4 to 0.5% w/w of magnesium stearate; and
from 0.1 to 2%, preferably from 0.2 to 1%, even more preferably from 0.5 to 0.6% w/w of sodium ascorbate.

The diameter of the uncoated tablet may be between 14.1 and 14.9 mm, preferably between 14.2 and 14.8 mm, more preferably between 14.3 and 14.7 mm.

The maximum thickness of the uncoated tablet may be between 6.2 and 7 mm, preferably between 6.3 and 6.9 mm, more preferably between 6.4 and 6.8 mm.

The friability of the uncoated tablet as measured according to the test method described herein may be less than 2.5%, preferably less than 2%, more preferably less than 1.6%.

The hardness of the uncoated tablet as measured according to the test method described herein may be between 20 and 100 N, more preferably between 40 and 70 N, even more preferably between 50 and 60 N.

The disintegration time of the uncoated tablet in water at 37° C. as measured according to the test method described herein may be less than 6 min, preferably less than 5 minutes 30, more preferably less than 5 minutes.

According to a preferred embodiment, the tablet according to the present invention is free of surfactant. Examples of surfactants that are traditionally used in tablets and that are not present in the composition of the invention are sodium lauryl sulfate, polysorbate 80, sorbitane monooleate. Indeed, contrary to what can be found in the prior art, Applicant has observed that surfactants are detrimental because they have an adverse effect on the dissolution and bioavailability of rifampicin.

According to another preferred embodiment, the tablet of the present invention is free of ethanol. Indeed, contrary to what can be found in prior art, Applicant has found that the tablets of the present invention can be prepared according to a process that uses water as the only solvent, specifically in the wet granulation step and in the film coating step, without observing degradation or drying problems.

The tablet according to the present invention may optionally comprise a film coating that further enhances the stability of the tablet overtime and facilitates the swallowing of the tablet for the patient. The film coating does not confer controlled release of the actives. The film coating is a conventional film coating, for example it may comprise talc, yellow iron oxide, soy lecithin, FD&C Blue #2/indigo carmine aluminium lake, polyvinyl alcohol, titanium dioxide and carmine. Such mixtures are commercially available from COLORCON, for example under the reference Opadry® II purple.

According to a preferred embodiment, the mass of the film-coated tablet is less than 1150 mg, preferably less than 1125 mg, and more preferably less than 1100 mg.

The diameter of the coated tablet may be between 14.2 and 15 mm, preferably between 14.3 and 14.9 mm, more preferably between 14.4 and 14.8 mm.

The maximum thickness of the coated tablet may be between 6.4 and 7.2 mm, preferably between 6.5 and 7.1 mm, more preferably between 6.6 and 7 mm.

The hardness of the coated tablet as measured according to the test method described herein may be between 100 and 150 N, more preferably between 110 and 140 N, even more preferably between 125 and 130 N.

The disintegration time of the coated tablet in water at 37° C. as measured according to the test method described herein may be less than 7 min, preferably less than 6 minutes 30, more preferably less than 6 minutes.

The dissolution time of the coated tablet which corresponds to the time it takes to dissolve 100% of the four actives, namely rifampicin, isoniazid, pyrazinamide and ethambutol in an aqueous medium as measured according to the test method described herein may be less than 45 minutes, preferably less than 40 minutes, more preferably less than 35 minutes.

The coated tablet is stable. By stable, it is meant that the quantity of each active ingredient and each impurity in the tablet is substantially identical after the tablet has been prepared and after the tablet has been aged for 2 months at 40° C. and 75% of relative humidity. By substantially identical, it is meant that the variation in quantity is less than 2%, preferably less than 1%. by weight Furthermore the coated tablet comprises less than 5%, preferably less than 4%, more preferably less than 3.5% by weight of total impurities relative to the weight of the coated tablet after it has been aged for 2 months at 40° C. and 75% of relative humidity. More specifically, the tablet comprises less than 1%, preferably less than 0.9%, more preferably less than 0.81% by weight of 3-formyl-rifampicine-isoniazid adduct responding to general formula (I) relative to the weight of the coated tablet after it has been aged for 2 months at 40° C. and 75% of relative humidity.

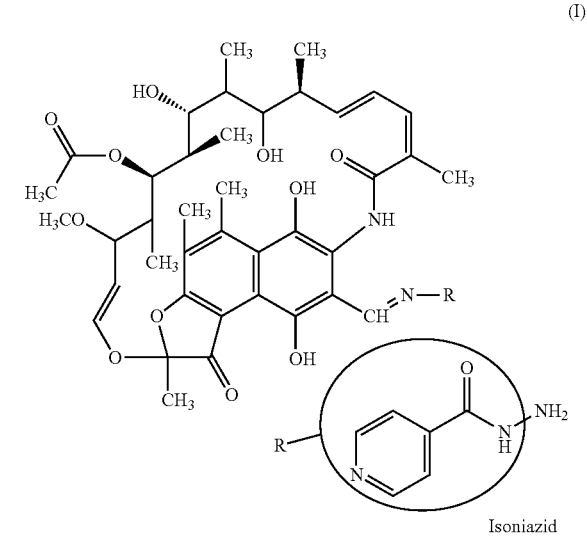

The tablets may be packed in any suitable packaging, for example in a double aluminium blister packaging, in order to obtain optimal stability conditions by avoiding exposure of the drug to direct sunlight.

The tablets according to the present invention may be obtained by a process comprising a step of a) wet-granulating isoniazid, pyrazinamide and ethambutol with an aqueous solution of a granulation binder to obtain granules.

The process according to the present invention may further comprise the following steps:
 b) milling the wet granules;
 c) drying the granules;
 d) reducing the particle size of the dried granules to less than 0.599 mm, preferably less than 0.5 mm, more preferably less than 0.422 mm;
 e) mixing the granules of step d) with rifampicine and extragranular excipients;
 f) compressing the mixture of step e) to obtain tablets
 g) optionally film-coating the tablets.

The operating conditions of the process may be carried out at a temperature of from 21 to 25° C. and at a relative humidity that is less than 60%.

According to an embodiment, the actives that are wet-granulated in step a) are previously sifted, for example through 0.599 mm sieves, and then dry-mixed in order to obtain a homogeneous mixture. For example, the sifted actives may be dry-mixed for a period of time between 10 and 30 minutes, preferably 20 minutes.

The wet-granulation step is carried out by contacting isoniazid, pyrazinamide and ethambutol in powder form with an aqueous solution of a granulation binder and by mixing. According to a specific embodiment, the quantity of aqueous solution of binder represents 8%, preferably 8.5% by weight based on the total weight of the dry constituents of the granule, namely isoniazid, pyrazinamide and ethambutol.

The wet granules are then milled in order to reduce their size and to uniformly distribute the water across the whole wet mass, for example by passing them through screens. Preferably, the screens used in the milling step are 4.0 mm screens.

The granules are then dried in order to remove the excess water. The granules may be dried in a suitable dryer, such as a fluid bed dryer. The inlet temperature of the dryer may be between 40 and 80° C., preferably between 50 and 70° C. According to a preferred embodiment, the granules are dried until a loss-on-drying (LOD) of less than 2%, preferably less than 1%, more preferably less than 0.5% w/w is achieved, as measured according to the test method described herein. The low value of LOD is advantageously obtained thanks to the low quantity of water that is used to prepare the granules.

Once the granules are dried, they are subjected to a size reduction in order to reach a particle size that is less than 0.599 mm, preferably less than 0.5 mm, more preferably less than 0.422 mm. For example, the granules can be sifted through a 0.599 mm, preferably 0.5 mm, more preferably 0.422 mm screen. In order to avoid losing too many granules, the granules that are retained by the screen can be milled, for example through a 1 mm screen and then passed though 0.599 mm, preferably 0.5 mm, more preferably 0.422 mm sieves.

The resulting granules are then mixed with the ingredients of the extragranular matrix, namely rifampicine and the extragranular excipients. According to a specific embodiment, where extragranular excipients comprise a disintegrant, a diluent, a lubricant and an antioxidant, the granules are first mixed with rifampicine, the diluent, the disintegrant and the antioxidant and the lubricant is added subsequently. Rifampicine, the diluent, the disintegrant and the antioxidant may be sifted, for example through 0.599 mm sieves, prior to their addition to the granules. The mixture comprising the granules, rifampicine, the diluent, the disintegrant and the antioxidant may be mixed for a time period of between 10 to 30 min, preferably 20 minutes. Once the mixture is homogeneous, the lubricant may be added. The lubricant may be sifted, for example through 0.251 mm sieves, prior to its addition to the mixture of granules, rifampicine, the diluent, the disintegrant and the antioxidant. The resulting mixture is blended for a time period of between 1 to 10 min, preferably 5 minutes.

The mixture is then compressed into tablets, for example with a tabletting press. According to a specific embodiment, the mixture is compressed using round standard concave bevelled-edge (SCBE) punches that are plain on both sides. The tablets that are obtained after compression thus exhibit a round bevelled-edge biconvex shape.

According to another embodiment, the compressed tablet may then film-coated. The film-coating step can be carried out in any suitable coating equipment such as an auto-coater by coating the tablet with an aqueous dispersion of a coating agent. Preferably, the coating is carried out at a temperature of from 30 to 60° C., preferably 40 to 50° C. The coating step is carried out until a weight gain of 4%, preferably 3.9%, even more preferably 3.81% is achieved.

According to a preferred embodiment, the process according to the invention comprises the following steps:
 a) sifting isoniazid, pyrazinamide, ethambutol or a pharmaceutically acceptable salt thereof and dry mixing the mixture;
 b) dissolving a granulation binder in water to obtain a granulation solution;
 c) wet granulating the mixture of step a) by wetting with the granulation solution of step b) to obtain granules;
 d) wet milling the granules;
 e) drying the granules;
 f) sifting the granules through 0.599 mm, preferably 0.5 mm, even more preferably 0.422 mm screen;
 g) sifting rifampicine, the diluent, the disintegrant and the antioxidant;
 h) mixing the granules of step f) with the mixture of step g);
 i) sifting the lubricant and adding to the mixture of step h);
 j) blending the mixture;
 k) compressing the mixture to obtain tablets;
 l) film-coating the tablets.

The present invention will be described with more details in the following examples which are provided for illustrative purposes only.

Test Methods

Particle Size

The particle size can be measured by using a vibratory sieve shaker comprising different sieve sizes arranged one above the other in descending order. A certain amount of granules is added on the top sieve and the apparatus vibrates for a fixed duration. The granules will be distributed amongst the sieves based on their size and the percentage of granules retained on each sieve can be calculated by weighing the sieve containing the retained granules.

Friability

The friability can be measured on a standard equipment known as a Friabilator. 20 tablets or 6 grams of tablet are weighed and loaded in the apparatus. The apparatus is rotated for 100 revolutions at 25 rpm. The tablets are unloaded from the apparatus, de-dusted and weighed. The percentage of friability can be determined by the formula:

(Weight before rotations−Weight of tablets after rotations)/Initial weight×100

Hardness

The hardness can be measured on a standard equipment known as a Hardness Tester. The tablet is placed between two arms, one arm being static and the other arm pushing the tablet against the static arm to crush the tablet. The pressure applied to crush the tablet is reported by the apparatus. The value is reported in Newtons or Kilopascals.

Disintegration Time

The disintegration time can be measured on a standard equipment comprising 6 tubes equipped with a 2 mm sieve at the bottom of each tube and filled with 900 mL of water having a pH of between 6 and 7 and a temperature of 37° C. A tablet is placed in each tube and the sieves are raised and lowered at a frequency of 30 dips per minute until the complete mass of the tablets disintegrates and passes through the 2 mm sieve.

The loss-on drying can be measured in a halogen moisture analyzer. 2 g of the granules are loaded in the apparatus which is maintained at 80° C. The loss-on-drying is determined and displayed by the analyzer.

Dissolution Time

The dissolution time of the actives can be measured by introducing one tablet (weight 1090 mg) in 900 mL of water at 37° C. buffered to pH 6.8 with a phosphate buffer wherein the medium is mixed with a paddle at 100 rpm. The phosphate buffer is prepared by dissolving 7 g of anhydrous dibasic sodium phosphate in 5 L of water, and adjusting with phosphoric acid to a pH of 6.8. The percentage of the actives dissolved at a given time can be measured by high performance liquid chromatography (HPLC).

EXAMPLES

Example 1: Composition According to the Invention

Table 1 below shows the quantity (in mg) of each ingredient in the tablet according to the present invention.

TABLE 1

| Ingredients | Quantity (mg per tablet) |
|---|---|
| Intra-granular | |
| Isoniazid | 75.00 |
| Pyrazinamide | 400.00 |
| Ethambutol Hydrochloride | 275.00 |
| Binder Solution | |
| Polyvinyl Pyrrolidone | 10.00 |
| Purified Water* | q.s. |
| Extra-granular | |
| Rifampicin | 150.00 |
| Microcrystalline Cellulose | 89.30 |
| Sodium Ascorbate | 5.70 |
| Croscarmellose Sodium | 40.00 |
| Magnesium Stearate | 5.00 |
| Total weight of Core tablets | 1050.00 |
| Film Coating | |
| Opadry II Purple 85G20180 | 40.00 |
| Purified Water* | q.s. |
| Total weight of Coated tablets | 1090.00 |

*Removed during drying, does not appear in the final product except in traces.

Procedure:

A. Preparation of Blend for Tablets

Step 1: Sift Isoniazid, Pyrazinamide and Ethambutol HCl through 0.599 mm sieve.

Step 2: Transfer the materials of Step 1, into Mixer Granulator and dry mix for 20 minutes with impeller slow speed and chopper slow speed Step 3: Dissolve polyvinylpyrrolidone in purified water with continuous stirring.

Step 4: Granulate the Step 2 material using solution of Step 3 until suitable granulation end point is obtained.

Step 5: Wet mill the granules through 4.0 mm screen and transfer the granules into the Fluid Bed Dryer, and dry the wet granules at inlet temperature of 60° C.±10° C. until LOD at 80° C. of below 1.0% w/w is achieved.

Step 6: Sift the dried granules through 0.422 mm screen, mill the retained granules through 1.0 mm screen and pass through 0.422 mm sieve to obtain granules wherein all of the granules have a particle size that is less than 0.422 mm. Record the yield of the granules and compensate the extra-granular materials as per yield.

Step 7: Sift Rifampicin, Sodium Ascorbate, Croscarmellose Sodium, and Microcrystalline Cellulose through 0.599 mm sieve.

Step 8: Blend Step 6 and Step 7 using Bin Blender for 20 min at 18 rpm±1 rpm.

Step 9: Sift Magnesium Stearate through 0.251 mm sieve and add to Step 8 materials present in the bin blender and lubricate the blend for 5 min at 18 rpm±1 rpm.

B. Compression of Tablets

Step 10: Compress the lubricated blend of step 9 using a Cadmach® Legacy tablet press with the following parameters: 45 station, single-stage, B-tooling (14.5 mm diameter, round, SCBE, plain on both sides).

C. Film Coating of Core Tablets

Step 11: Disperse Opadry® II Purple 85G20180 in purified water with continuous stirring for 45 minutes.

Step 12: Load the tablets into Auto coater and warm the tablets at suitable pan rpm by keeping sufficient inlet and exhaust temperature to achieve the bed temperature of 40 to 50° C.

Step 13: Coat the tablets of step 2 using step 1 dispersion at suitable pan rpm, suitable gun to bed distance, sufficient inlet and exhaust temperature and suitable spray rate maintaining the tablet bed temperature of 40 to 50° C.

Step 14: Continue the coating until the weight gain of 3.81% is achieved.

Particle Size Distribution of the Granules:

The particle sizes listed in Table 2 are obtained according to the Test methods described herein.

TABLE 2

| Aperture Size | % of granules retained | Cumulative % of granules retained |
|---|---|---|
| 710μ | 0.40 | 0.40 |
| 500μ | 4.37 | 4.77 |
| 355μ | 10.74 | 15.51 |
| 250μ | 11.93 | 27.44 |
| 180μ | 14.31 | 41.75 |
| 150μ | 9.54 | 51.29 |
| 125μ | 12.13 | 63.42 |
| 90μ | 17.50 | 80.91 |
| Below 90μ | 19.09 | 100.00 |

Physical Parameters:

The parameters listed in Table 3 are obtained for the uncoated and the coated tablets according to the Test methods described herein.

TABLE 3

| | |
|---|---|
| Diameter of uncoated tablet | 14.5 mm ± 0.2 mm |
| Diameter of coated tablet | 14.6 mm ± 0.2 mm |
| Average weight of uncoated tablet | 1050 mg ± 3% |
| Average weight of coated tablet | 1090 mg ± 3% |
| Hardness of uncoated tablet | 50-60 N |
| Hardness of coated tablet | 125-130 N |
| Friability of uncoated tablet | 0.15% w/w |
| Thickness of uncoated tablet | 6.6 mm ± 0.2 mm |
| Thickness of coated tablet | 6.8 mm ± 0.2 mm |
| Disintegration Time of uncoated tablet | 4 min 30 sec to 5 min |
| Disintegration Time of coated tablet | 5 min 30 sec to 6 min |

Stability:

Table 4 shows the percentage of active ingredient that is effectively measured relative to the target quantity of active ingredients that are present in the coated tablets immediately after the tablets are prepared as well as after aging of the tablets for 1 month and 2 months at 40° C. and 75% relative humidity.

TABLE 4

| | | Limits | Initial | Aging at 40° C. and 75% relative humidity (%) | |
|---|---|---|---|---|---|
| | | (%) | (%) | 1 month | 2 months |
| Active ingredients | Rifampicin | 90-105 | 101.3 | 101.4 | 102.0 |
| | Isoniazid | 90-105 | 100.0 | 97.8 | 98.20 |
| | Pyrazinamide | 90-105 | 101.3 | 101.2 | 100.5 |
| | Ethambutol HCl | 90-105 | 100.6 | 100.3 | 101.4 |

Table 5 shows the weight percentage of impurities based on the weight of the coated tablet that are present in the coated tablets immediately after the tablets are prepared as well as after aging of the tablets for 1 month and 2 months at 40° C. and 75% relative humidity.

TABLE 5

| | | Limits | Initial | Aging at 40° C. and 75% relative humidity (%) | |
|---|---|---|---|---|---|
| | | (%) | (%) | 1 month | 2 months |
| Related impurities | Rifampicin quinone | <1.5 | 0.784 | 0.962 | 0.967 |
| | Rifampicin N-oxide | <0.5 | 0.393 | 0.457 | 0.477 |
| | 3-Formyl Rifampicin | <0.5 | 0.068 | 0.060 | 0.082 |
| | 3-Formyl-Rifampicin-Isoniazid adduct | <4.0 | 0.615 | 0.631 | 0.802 |
| | 25 Desacetyl-Rifampicin | <0.5 | 0.117 | 0.148 | 0.149 |
| Other related impurities | Single specified (retention time 0.35) | <0.5 | 0.294 | 0.323 | 0.322 |
| | Single specified (retention time 0.80) | <0.5 | 0.206 | 0.235 | 0.238 |
| | Single unidentified | <0.2 | 0.126 | 0.146 | 0.145 |
| | Total Impurities | <8.0 | 2.803 | 3.291 | 3.506 |

As such, the tablet obtained according to the invention is stable in time and the total level of impurities is much lower than the required standard. Specifically, the percentage of 3-formyl-Rifampicine-Isoniazid adduct in the tablet is very low which confirms that there is hardly any adverse interaction between rifampicine and isoniazid.

Table 6 shows the loss on drying and the dissolution time of the coated tablets immediately after the tablets are prepared as well as after aging of the tablets for 1 month and 2 months at 40° C. and 75% relative humidity.

TABLE 6

| | | Limits | Initial | Aging at 40° C. and 75% relative humidity (%) | |
|---|---|---|---|---|---|
| | | (%) | (%) | 1 month | 2 months |
| Loss on drying | | <3.0% | 1.12 | 0.87 | 0.81 |
| % of dissolved actives at 45 min after beginning the Dissolution time test pH 6.8 phosphate buffer 900 mL paddle 100 rpm | Rifampicin | >75% | 101 | 101 | 100 |
| | Isoniazid | >75% | 98 | 98 | 100 |
| | Pyrazinamide | >75% | 102 | 102 | 102 |
| | Ethambutol HCl | >75% | 100 | 100 | 99 |

Table 7 gives the cumulative percentage of each active released according to the Dissolution time test disclosed herein.

TABLE 7

| | 5 min | 10 min | 15 min | 20 min | 30 min | 45 min | 60 min |
|---|---|---|---|---|---|---|---|
| Rifampicin | 47 | 74 | 86 | 93 | 98 | 100 | 100 |
| Isoniazid | 86 | 99 | 100 | 100 | 100 | 100 | 100 |
| Pyrazinamide | 90 | 101 | 102 | 102 | 102 | 102 | 102 |
| Ethambutol | 84 | 99 | 99 | 99 | 99 | 99 | 99 |

As such, the tablet obtained according to the invention is stable in time and the loss on drying and the dissolution time are within the required standards.

Comparative Example—Replacement of Disintegrant

An uncoated tablet was prepared as disclosed in Example 1 except that the 40 mg of Croscarmellose Sodium are replaced with 40 mg of Crospovidone.

The parameters listed in table 8 are obtained for the tablet according to the Test methods described herein:

TABLE 8

| | |
|---|---|
| Hardness of tablet | 60 N |
| Friability of tablet | 0.3% w/w |
| Disintegration time of tablet | 6 min to 7 min |

As such, the replacement of croscarmellose sodium by crospovidone leads to a greater friability and dissolution time of the tablet compared to the tablet according to Example 1.

Comparative Example—Different Granule Size

An uncoated tablet was prepared as disclosed in Example 1 except that in step 6 of the process of preparation, the granules are sifted through 0.853 mm screen instead of 0.422 mm screen. As such, the particle size of all of the resulting comparative granules is less than 0.853 mm.

The parameters listed in table 9 are obtained for the tablet according to the Test methods described herein:

TABLE 9

| | |
|---|---|
| Hardness of tablet | 50 N |
| Friability of tablet | failed: tablets break after 100 rotations |
| Disintegration time of tablet | 7 min |

As such, the change in granule size leads a decrease in the hardness of the tablet and to a greater dissolution time of the tablet compared to the tablet according to Example 1. Furthermore, the comparative tablet that is obtained is too friable to be coated.

The invention claimed is:

1. A monolayer tablet for use in treatment of tuberculosis comprising a mixture of:
   granules comprising isoniazid, pyrazinamide, ethambutol or a pharmaceutically acceptable salt thereof, and at least one granulation binder;
   rifampicine in powder form; and
   extragranular excipients,
   wherein all of the granules have a particle size that is less than 0.5 mm.

2. The monolayer tablet according to claim 1, wherein the monolayer tablet exhibits a mass less than 1,100 mg.

3. The monolayer tablet according to claim 1, comprising 75 mg of isoniazid, 400 mg of pyrazinamide, 275 mg of ethambutol hydrochloride, and 150 mg of rifampicine.

4. The monolayer tablet according to claim 1, wherein the at least one granulation binder is selected from the group consisting of povidone, polyvinyl alcohol, maize starch, and pregelatinized starch.

5. The monolayer tablet according to claim 1, wherein the monolayer tablet comprises from 0.1 to 2% w/w of the at least one granulation binder.

6. The monolayer tablet according to claim 1, wherein the extragranular excipients comprise a disintegrant selected from the group consisting of croscarmellose sodium, crospovidone, maize starch, low substituted hydroxypropyl cellulose, and alginic acid.

7. The monolayer tablet according to claim 1, wherein the extragranular excipients comprise a diluent, an antioxidant, a lubricant, a flavouring agent, a colorant, or mixtures of the foregoing.

8. The monolayer tablet according to claim 1, wherein the monolayer tablet comprises from 10 to 17% w/w of the extragranular excipients.

9. The monolayer tablet according to claim 7, wherein the lubricant is selected from the group consisting of magnesium stearate, sodium stearylfumarate, calcium stearate, stearic acid, zinc stearate, and glyceryl behanate.

10. The monolayer tablet according to claim 7, wherein the monolayer tablet comprises from 0.1 to 2% w/w of the lubricant.

11. The monolayer tablet according to claim 7, wherein the antioxidant is selected from the group consisting of sodium ascorbate, 2,6-di-tert-butyl-4-hydroxytoluene (BHT), citric acid, tocopherol, and sodium metabisulfite.

12. The monolayer tablet according to claim 7, wherein the monolayer tablet comprises from 0.1 to 2% w/w of the antioxidant.

13. The monolayer tablet according to claim 1, wherein the monolayer tablet is free of surfactant.

14. The monolayer tablet according to claim 1, wherein the monolayer tablet further comprises a film coating.

15. The monolayer tablet according to claim 14, wherein the monolayer tablet exhibits a mass less than 1,150 mg.

16. The monolayer tablet according to claim 14 wherein the monolayer tablet comprises less than 5% by weight of total impurities relative to the weight of the monolayer tablet after the monolayer tablet has been aged for 2 months at 40° C. and 75% relative humidity.

17. The monolayer tablet according to claim 14, wherein the monolayer tablet comprises less than 1% by weight of 3-formyl-rifampicine-isoniazid adduct of formula (I)

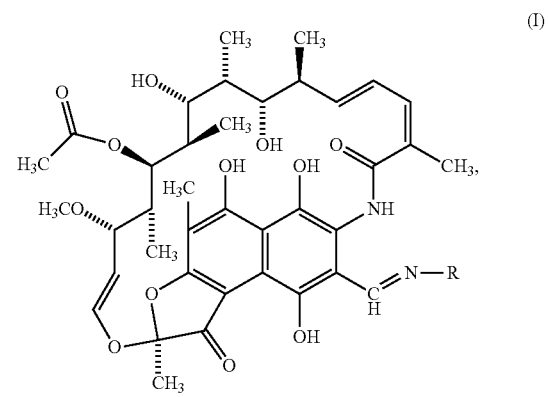

(I)

wherein R is isoniazid, relative to the weight of the monolayer tablet after the monolayer tablet has been aged for 2 months at 40° C. and 75% relative humidity.

18. A process for preparing the monolayer tablet according to claim 1, comprising a step of wet-granulating isoniazid, pyrazinamide, and ethambutol or a pharmaceutically acceptable salt thereof with an aqueous solution of a granulation binder to obtain granules.

19. The monolayer tablet according to claim 1, wherein all of the granules have a particle size which further is more than 0.075 mm.

20. The monolayer tablet according to claim 1, wherein all of the granules have a particle size that is less than 0.422 mm.

* * * * *

Disclaimer

9,814,711 B2 — Kumar Amith, Gurdaspur (IN); Madavan Bindu, Paris (FR); Prasad Kum, Hyderabad (IN); Khullar Praveen, Dona Paula (IN). ANTITUBERCULAR COMPOSITION COMPRISING RIFAMPICIN, ISONIAZID, ETHAMBUTOL AND PRYRANZINAMIDE AND ITS PROCESS OF PREPARATION. Patent dated November 14, 2017. Disclaimer filed May 26, 2020, by the assignee, Sanofi.

Hereby disclaim complete entire claims 1-20 of said patent.

*(Official Gazette, June 30, 2020)*